(12) United States Patent
Kobayashi

(10) Patent No.: US 10,271,818 B2
(45) Date of Patent: Apr. 30, 2019

(54) IMAGE PROCESSING APPARATUS, METHOD OF CONTROLLING IMAGE PROCESSING APPARATUS, PROGRAM, AND STORAGE MEDIUM

(71) Applicant: TERUMO KABUSHIKI KAISHA, Tokyo (JP)

(72) Inventor: Youhei Kobayashi, Hadano (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 0 days.

(21) Appl. No.: 14/865,227

(22) Filed: Sep. 25, 2015

(65) Prior Publication Data

US 2016/0093049 A1 Mar. 31, 2016

(30) Foreign Application Priority Data

Sep. 25, 2014 (JP) .................................. 2014-195753

(51) Int. Cl.
| | |
|---|---|
| *G06T 7/33* | (2017.01) |
| *G06T 7/38* | (2017.01) |
| *A61B 8/08* | (2006.01) |
| *A61B 8/12* | (2006.01) |

(Continued)

(52) U.S. Cl.
CPC .......... *A61B 8/0891* (2013.01); *A61B 5/0035* (2013.01); *A61B 5/0066* (2013.01); *A61B 5/0084* (2013.01); *A61B 5/02007* (2013.01); *A61B 5/6852* (2013.01); *A61B 5/6876* (2013.01); *A61B 5/7257* (2013.01); *A61B 8/12* (2013.01); *A61B 8/5261* (2013.01); *G06T 7/337* (2017.01); *G06T 7/38* (2017.01); *G06T 2207/10068* (2013.01);

(Continued)

(58) Field of Classification Search
None
See application file for complete search history.

(56) References Cited

U.S. PATENT DOCUMENTS

| | | | |
|---|---|---|---|
| 8,208,995 B2* | 6/2012 | Tearney ............... | A61B 5/0062 600/476 |
| 8,538,508 B2* | 9/2013 | Redel .................. | A61B 5/0066 600/407 |
| 9,076,202 B2* | 7/2015 | Courtney ............. | A61B 5/0066 |

(Continued)

FOREIGN PATENT DOCUMENTS

JP 11-56752 A 3/1999

*Primary Examiner* — Nancy Bitar
(74) *Attorney, Agent, or Firm* — Buchanan Ingersoll & Rooney PC

(57) ABSTRACT

An image processing apparatus and method are disclosed, which processes an image of a target object. The image processing apparatus includes an image acquisition unit which acquires a series of first images and a series of second images of the target object which are scanned at a first pull-back speed and at a second pull-back speed faster than the first pull-back speed, a correlation unit which correlates first images, which are scanned at the first pull-back speed, with first images, which are scanned at the second pull-back speed, and a control unit which correlates a series of the first images which are scanned at the first pull-back speed and a series of the second images which are scanned at the second pull-back speed so as to display the images on a display apparatus, based on the result of the correlation.

20 Claims, 10 Drawing Sheets

(51) Int. Cl.
*A61B 5/00* (2006.01)
*A61B 5/02* (2006.01)

(52) U.S. Cl.
CPC ............... *G06T 2207/10101* (2013.01); *G06T 2207/10132* (2013.01); *G06T 2207/30101* (2013.01)

(56) References Cited

U.S. PATENT DOCUMENTS

| | | | |
|---|---|---|---|
| 9,254,102 B2 * | 2/2016 | Tearney | A61B 5/0062 |
| 2007/0232892 A1 * | 10/2007 | Hirota | A61B 5/0066 600/407 |
| 2008/0161696 A1 * | 7/2008 | Schmitt | A61B 5/0066 600/467 |
| 2009/0073454 A1 * | 3/2009 | Ozawa | A61B 5/0066 356/477 |
| 2009/0264768 A1 * | 10/2009 | Courtney | A61B 5/0062 600/463 |
| 2010/0249588 A1 * | 9/2010 | Knight | A61B 8/12 600/437 |
| 2012/0035454 A1 * | 2/2012 | Tearney | A61B 5/0062 600/407 |
| 2012/0215091 A1 * | 8/2012 | Suzuki | A61B 5/0066 600/407 |
| 2012/0253185 A1 * | 10/2012 | Furuichi | A61B 5/0066 600/425 |
| 2013/0012811 A1 * | 1/2013 | Schmitt | A61B 5/0066 600/427 |
| 2013/0216114 A1 * | 8/2013 | Courtney | A61B 5/0066 382/130 |

* cited by examiner

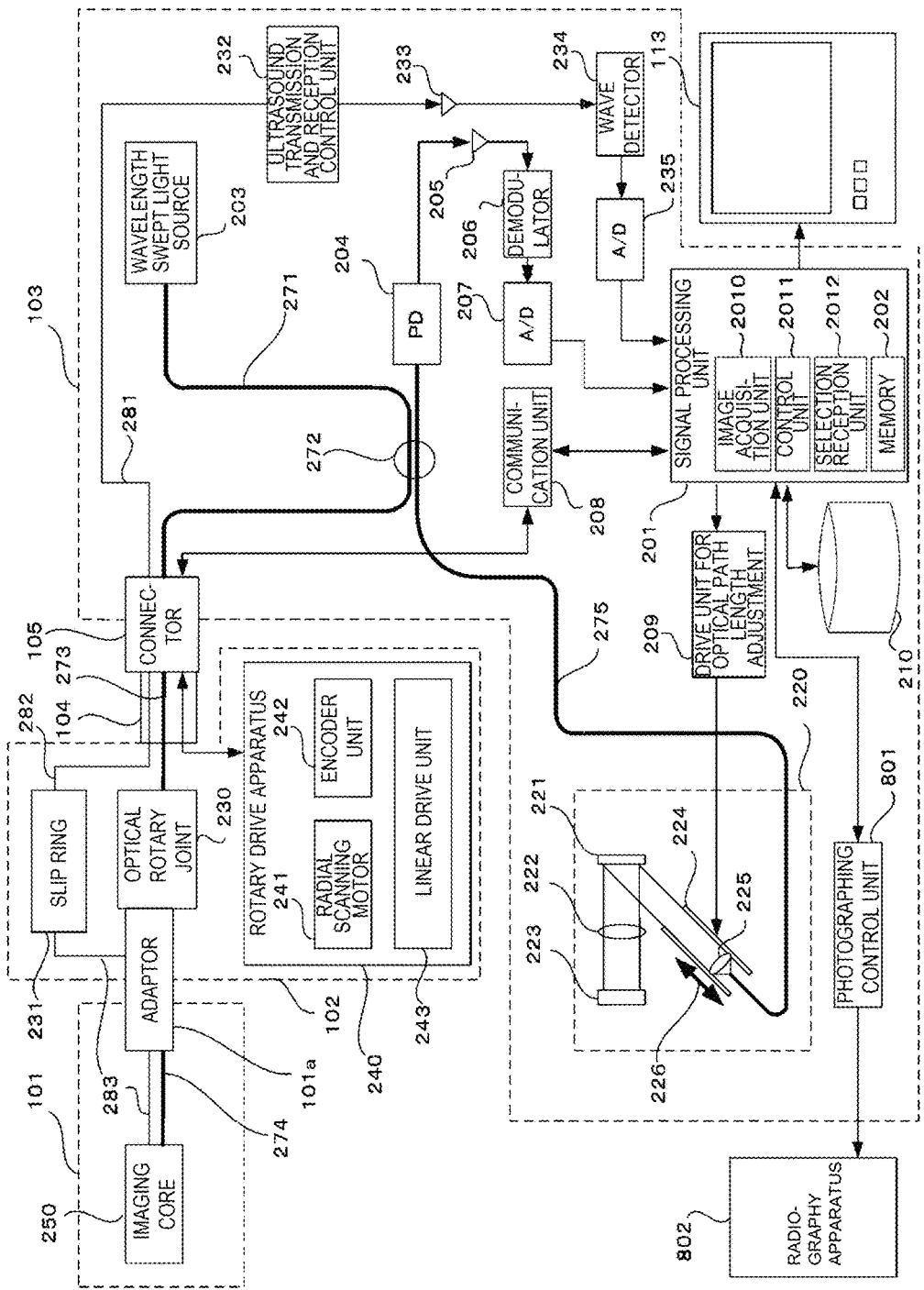

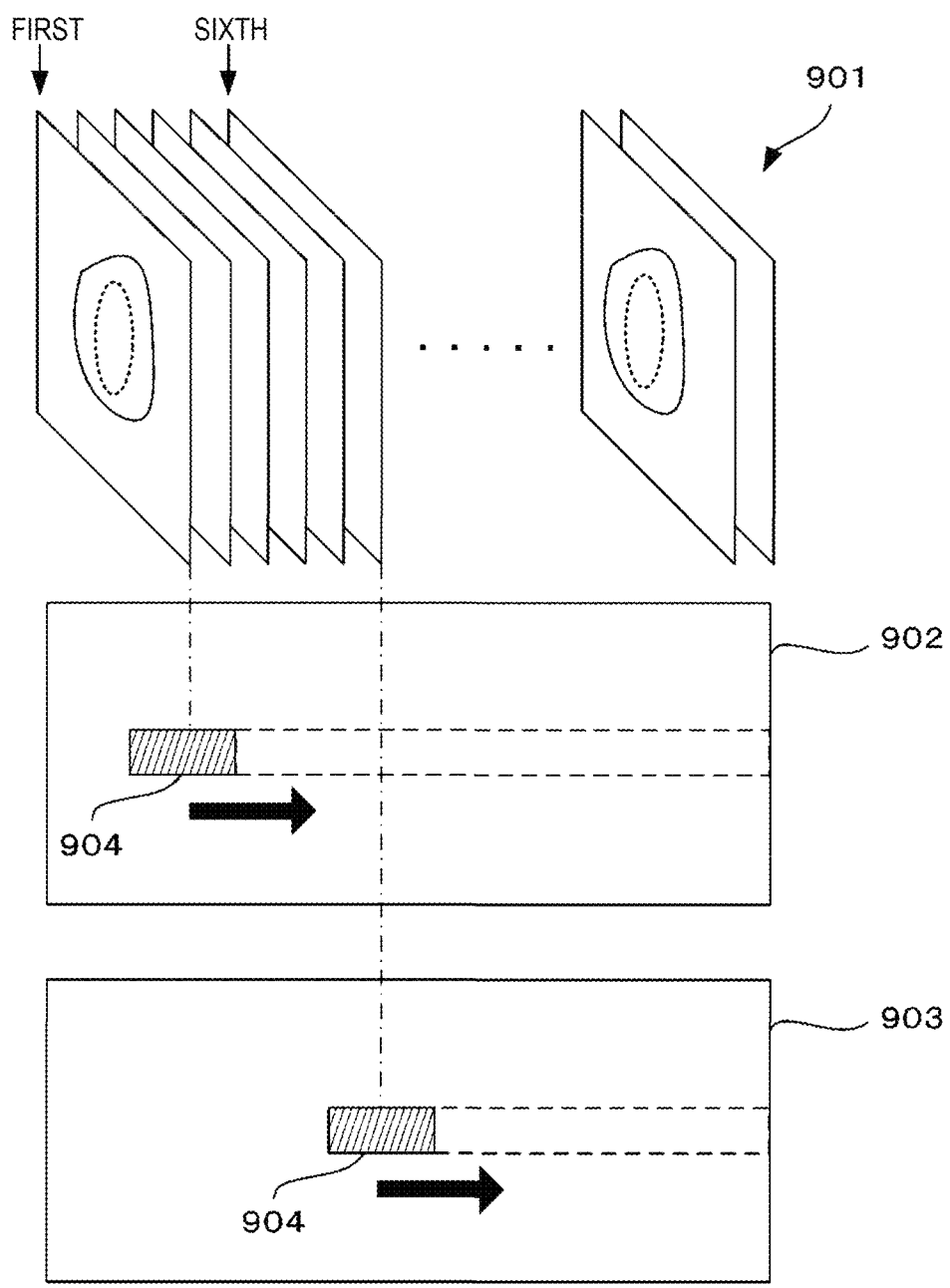

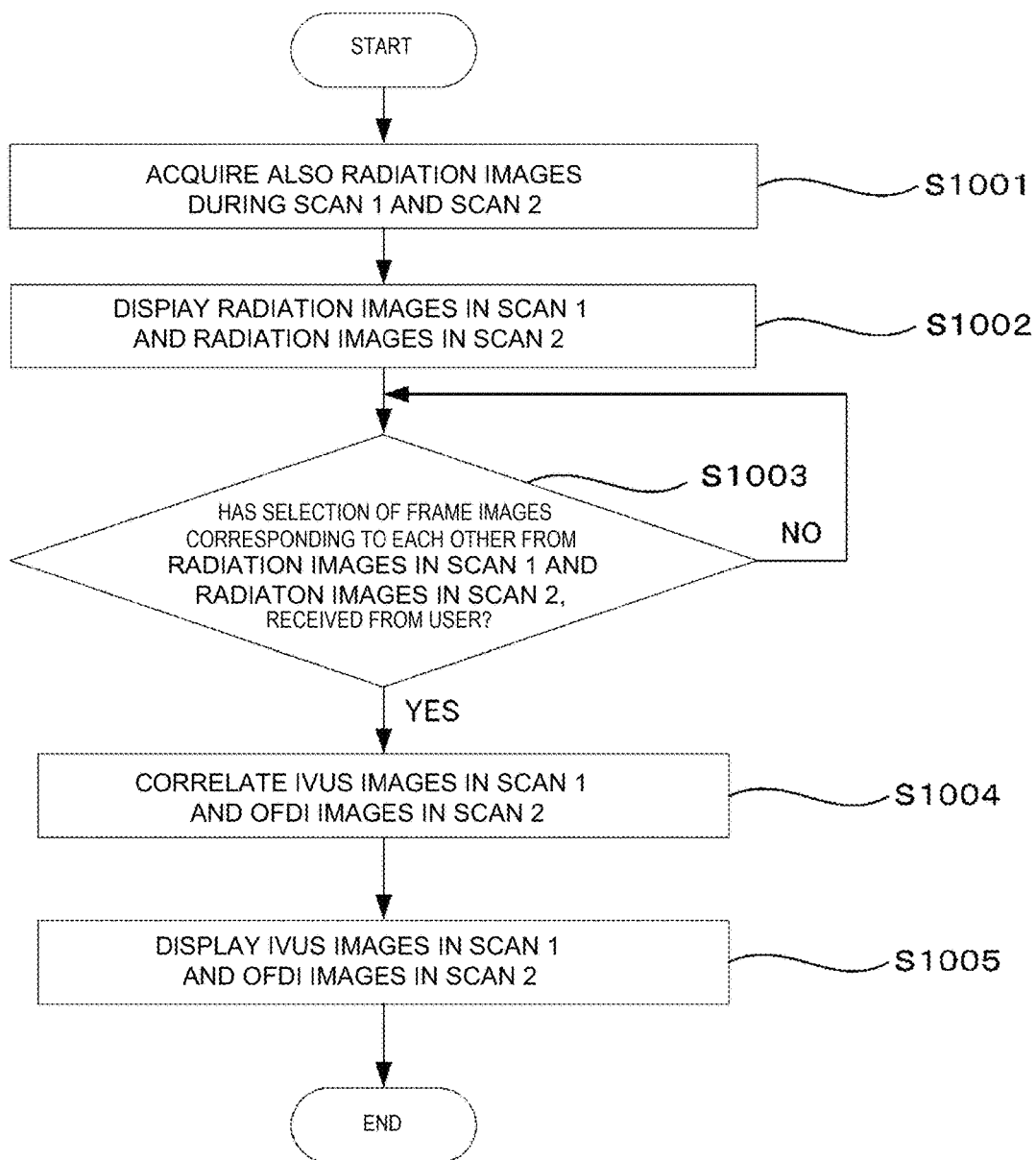

IMAGE PROCESSING APPARATUS, METHOD OF CONTROLLING IMAGE PROCESSING APPARATUS, PROGRAM, AND STORAGE MEDIUM

CROSS-REFERENCES TO RELATED APPLICATIONS

This application claims priority to Japanese Patent Application No. 2014-195753 filed on Sep. 25, 2014, the entire content of which is incorporated herein by reference.

TECHNICAL FIELD

The present disclosure generally relates to an image processing apparatus, a method of controlling the image processing apparatus, a program, and a storage medium.

BACKGROUND DISCUSSION

When percutaneously treating a stenosed site which can cause, for example, myocardial infarction that occurs in a biological lumen such as a blood vessel, a vessel or the like, a diagnostic catheter can be used which acquires an image of a biological lumen using an inspection wave such as an ultrasound or light, in order to observe the properties of the stenosed site or the state of the stenosed site after treatment.

In intravascular ultrasound (IVUS) diagnosis, an imaging core which has an ultrasound transducer is rotatably provided at a distal end of an insertion portion and is inserted into a lumen in a living body, and then, performs scanning (radial scanning) while rotating through a drive shaft or the like which extends from a driving unit on a hand side.

In addition, in optical frequency domain imaging (OFDI) using wavelength sweep, radial scanning can be performed in a blood vessel by inserting an optical probe unit, into which an imaging core is interpolated to which an optical lens and an optical mirror (transmitting and receiving unit) is attached at a distal end of an optical fiber, into the blood vessel; emitting measurement light into the blood vessel from the transmitting and receiving unit at the distal end while rotating the imaging core; and receiving reflected light from a biological tissue. Moreover, a tomographic image of the blood vessel can be drawn based on interference light generated by allowing the received reflected light to interfere with reference light.

In the OFDI, an image with a relatively high resolution with respect to the lumen surface of a blood vessel can be obtained. However, only an image up to a tissue which is comparatively shallower from the lumen surface of a blood vessel is obtained. In contrast, in the case of the IVUS, an image of a vascular tissue which is deeper than that in the OFDI can be obtained, while the resolution of an obtained image is lower than that of the OFDI. In recent years, an imaging apparatus for diagnosis has been proposed which has an imaging core equipped with a dual sensor in which the function of the IVUS and the function of the OFDI are combined (refer to JP-A-11-56752).

With such an apparatus, a medical practitioner can evaluate an identical observation site using images including both the IVUS images and the OFDI images. For both of the IVUS and OFDI images, a plurality of tomographic images are acquired while performing a pull-back operation (operation of moving the imaging core to the hand side). Low speed pull-back (for example, 0.5 mm/sec) and high speed pull-back (for example, 20 mm/sec) are used together by switching the movement speed (pull-back speed) of the imaging core. In general, the quality of the image acquired through high speed pull-back is more deteriorated than that of the image acquired through low speed pull-back. For this reason, if possible, it is preferable to acquire an image through low speed pull-back. However, in the case of the low speed pull-back, it may be difficult to acquire an image through OFDI since it is impossible to continue flushing. In contrast, an image through IVUS can be acquired in all of the cases of the low speed pull-back and the high speed pull-back.

It may be necessary to evaluate an identical observation site using IVUS images which are acquired through low speed pull-back and OFDI images which are acquired through high speed pull-back.

However, the IVUS and the OFDI are modalities (imaging devices) different from each other. Therefore, it may be difficult to align IVUS images which are acquired through low speed pull-back and OFDI images which are acquired through high speed pull-back with respect to an identical observation site. In this manner, it can be difficult to align the images using different modalities. The present disclosures provide a technique that facilitates the alignment between images using different modalities.

SUMMARY

An image processing apparatus is disclosed, which can include an image of a target object, including an image acquisition section which is configured to acquire a series of first images and a series of second images of the target object which are scanned at a first pull-back speed and at a second pull-back speed faster than the first pull-back speed, a control section which is configured to display a series of the first images which are scanned at the first pull-back speed and a series of the first images which are scanned at the second pull-back speed, on the display apparatus; and a selection reception section which is configured to receive a selection of the first images which are scanned at the first pull-back speed and the first images which are scanned at the second pull-back speed, from the images displayed on the display apparatus, from a user, in which the control section is configured to correlate a series of the first images which are scanned at the first pull-back speed and a series of the second images which are scanned at the second pull-back speed so as to display the images on the display apparatus, based on the selection.

An image processing apparatus is disclosed which processes an image of a target object, comprising: an image acquisition section which is configured to acquire a series of first images and a series of second images of the target object which are scanned at a first pull-back speed and at a second pull-back speed faster than the first pull-back speed; a correlation section which is configured to correlate first images, which are scanned at the first pull-back speed, with first images, which are scanned at the second pull-back speed; and a control section which is configured to correlate a series of the first images which are scanned at the first pull-back speed and a series of the second images which are scanned at the second pull-back speed so as to display the images on a display apparatus, based on the result of the correlation.

An image processing apparatus is disclosed, which processes an image of a target object, comprising: an image acquisition section which is configured to acquire a series of first images of the target object and a series of second images of the target object which are scanned at a first pull-back speed and at a second pull-back speed faster than the first pull-back speed, and a series of third images of the target object which are scanned in synchronization with a series of the first images and a series of the second images; a correlation section which is configured to correlate third images, which are scanned at the first pull-back speed, with third images, which are scanned at the second pull-back speed; and a control section which is configured to correlate a series of the first images which are scanned at the first pull-back speed and a series of the second images which are scanned at the second pull-back speed so as to display the images on a display apparatus, based on the result of the correlation.

A method is disclosed of controlling an image processing apparatus which processes an image of a target object, the method comprising: acquiring a series of first images and a series of second images of the target object which are scanned at a first pull-back speed and at a second pull-back speed faster than the first pull-back speed; correlating first images, which are scanned at the first pull-back speed, with first images, which are scanned at the second pull-back speed; and correlating a series of the first images which are scanned at the first pull-back speed and a series of the second images which are scanned at the second pull-back speed so as to display the images on a display apparatus, based on the result of the correlation.

A method is disclosed of controlling an image processing apparatus which processes an image of a target object, the method comprising: acquiring a series of first images of the target object and a series of second images of the target object which are scanned at a first pull-back speed and at a second pull-back speed faster than the first pull-back speed, and a series of third images of the target object which are scanned in synchronization with a series of the first images and a series of the second images; correlating third images, which are scanned at the first pull-back speed, with third images, which are scanned at the second pull-back speed; and correlating a series of the first images which are scanned at the first pull-back speed and a series of the second images which are scanned at the second pull-back speed so as to display the images on a display apparatus, based on the result of the correlation.

According to the present disclosure, the alignment between images using different modalities becomes relatively easy.

BRIEF DESCRIPTION OF THE DRAWINGS

FIG. 8 is a view showing a configuration example of an imaging apparatus for diagnosis (image processing apparatus and its peripheral devices) according to the second exemplary embodiment.

FIG. 9 is a view illustrating a relationship between a radiation image and an image, which is scanned by an imaging core according to a third exemplary embodiment.

FIG. 10 is a flowchart showing a processing procedure of image alignment (alignment of IVUS images in scan 1 and OFDI images in scan 2) according to the third exemplary embodiment.

DETAILED DESCRIPTION

Hereinafter, each exemplary embodiment of the present disclosure will be described in detail while referring to the accompanying drawings. Note that the exemplary embodiments described below are favorable specific examples of the present disclosure, and therefore, are technically preferably limited in various ways. However, the scope of the present disclosure is not limited to these modes as long as there is no particular description of limiting the present disclosure in the following description.

An imaging apparatus for diagnosis according to the present exemplary embodiment will be described as an imaging apparatus for diagnosis which has an IVUS function and an OFDI function.

1. Appearance Configuration of Imaging Apparatus for Diagnosis

Figure 1:
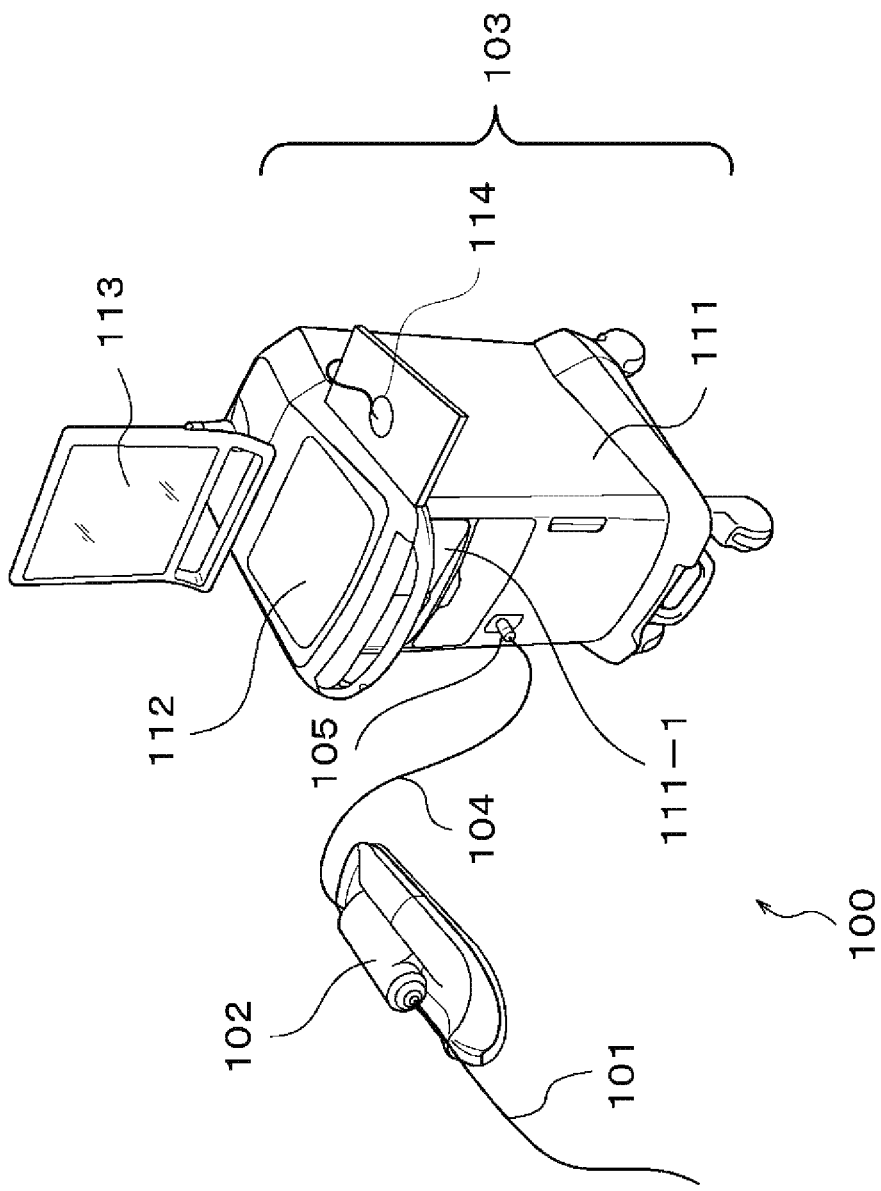
FIG. 1 is a view showing an appearance configuration of an imaging apparatus for diagnosis according to an exemplary embodiment of the present disclosure.

FIG. 1 is a view showing an appearance configuration of an imaging apparatus for diagnosis 100 according to an exemplary embodiment of the present disclosure. As shown in FIG. 1, the imaging apparatus for diagnosis 100 can include a probe 101, a scanner and pull-back unit 102, an image processing apparatus 103, and a display apparatus 113. The scanner and pull-back unit 102 and the image processing apparatus 103 are connected by a cable 104, in which a signal line or an optical fiber is accommodated, through a connector 105. Note that the image processing apparatus 103 and the display apparatus 113 are described as separate bodies in the present exemplary embodiment, but a configuration in which the image processing apparatus 103 includes the display apparatus 113 may also be employed.

The probe 101 is directly inserted into a blood vessel. A catheter accommodating an imaging core, which includes an ultrasound transmitting and receiving unit that transmits an ultrasound based on a pulse signal and receives a reflected wave from the inside of the blood vessel, and an optical transmitting and receiving unit which continuously transmits the transmitted light (measurement light) into the blood vessel and continuously receives reflected light from the inside of the blood vessel, is interpolated to the probe. The imaging apparatus for diagnosis 100 measures the condition of the inside of the blood vessel using the imaging core.

The probe 101 is detachably attached to the scanner and pull-back unit 102 which specifies an operation in an axial direction and an operation in a rotational direction, in a blood vessel, of the imaging core in the catheter which is interpolated to the probe 101 by driving an embedded motor. In addition, the scanner and pull-back unit 102 acquires a signal of a reflected wave which is received in the ultrasound transmitting and receiving unit in the imaging core and reflected light which is received in the optical transmitting and receiving unit, and transmits the acquired signal and the reflected light to the image processing apparatus 103.

The image processing apparatus 103 has a function for inputting various set values when measurement is performed, and a function for processing ultrasound data or interference light data which is obtained through measurement and displaying various blood vessel images.

In the image processing apparatus 103, the reference numeral 111 is a main body control unit. The main body control unit 111 generates line data from a signal of a reflected wave of an ultrasound which is obtained through measurement; and generates an ultrasound tomographic image (IVUS image) through interpolation processing. Furthermore, the main body control unit 111 generates interference light data by causing reflected light from the imaging core to interfere with reference light which is obtained by separating light from a light source, generates line data based on the interference light data, and generates an optical tomographic image (OFDI image) of a blood vessel based on light interference through the interpolation processing.

The reference numeral 111-1 is a printer and DVD recorder which prints a processing result in the main body control unit 111 or stores the processing result as data. The reference numeral 112 is an operation panel, and a user inputs various set values and instructions through the operation panel 112. The reference numeral 113 is an LCD monitor as a display apparatus and displays various cross-sectional images generated in the main body control unit 111. The reference numeral 114 is a mouse as a pointing device (coordinate input device).

2. Functional Configuration of Imaging Apparatus for Diagnosis (Mainly Image Processing Apparatus)

Next, a functional configuration of the imaging apparatus for diagnosis 100 (mainly the image processing apparatus 103) will be described.

Figure 2:
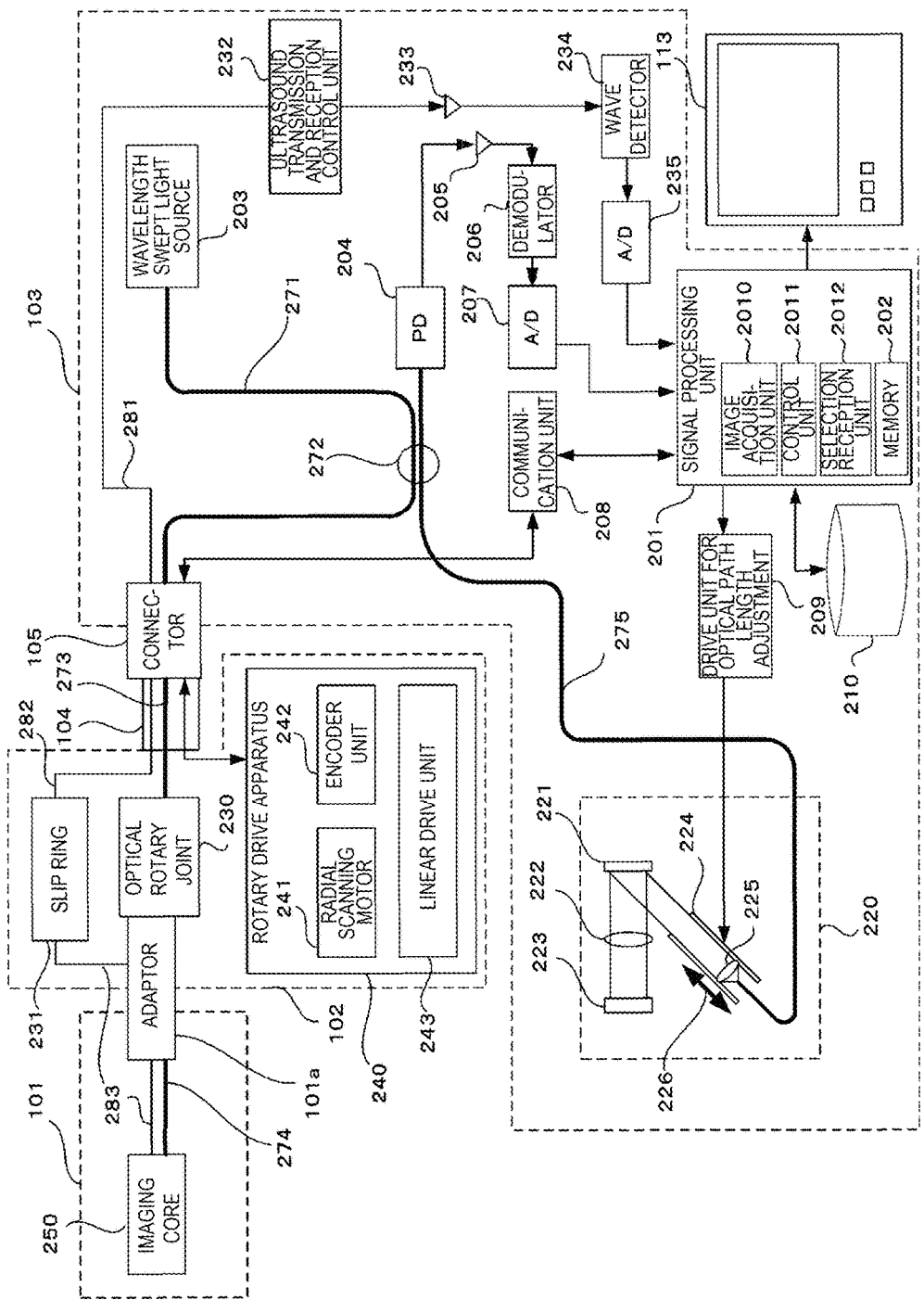
FIG. 2 is a view showing a configuration of an imaging apparatus for diagnosis (image processing apparatus and its peripheral devices) according to the exemplary embodiment of the present disclosure.

FIG. 2 is a block configuration view of the imaging apparatus for diagnosis 100. Hereinafter, the functional configuration for realizing wavelength sweep type optical frequency domain imaging (OFDI) will be described using the drawing.

In the drawing, the reference numeral 201 is a signal processing unit which manages the overall control of the imaging apparatus for diagnosis, and is constituted of several circuits starting with a microprocessor. The reference numeral 210 is a non-volatile storage device which is represented by a hard disk and in which various programs or data files which are executed by the signal processing unit 201 are stored. The reference numeral 202 is a memory (RAM) which is provided in the signal processing unit 201. The reference numeral 203 is a wavelength swept light source and is a light source which repeatedly generates light of a wavelength which varies within a predetermined range along a time axis. Here, the reference numeral 2010 is an image acquisition unit which acquires an ultrasound tomographic image (IVUS image) or an optical tomographic image (OFDI image) which are scanned by an imaging core 250 to be described later. The reference numeral 2011 is a control unit which performs various kinds of processing and controls the display on the display apparatus 113. The reference numeral 2012 is a selection reception unit which receives an input from a user through the display apparatus 113, the mouse 114, in a case where the operation panel 112 and the display apparatus 113 having, for example, a touch function, and performs selection of an image.

Light output from the wavelength swept light source 203 is incident on one end of a first single mode fiber 271 and is transmitted to a distal side. The first single mode fiber 271 is optically bound to a fourth single mode fiber 275 in an optical fiber coupler 272 in the middle of the fibers.

Light which has been incident on the first single mode fiber 271 and has been emitted to the distal side from the optical fiber coupler 272 is guided to a second single mode fiber 273 through the connector 105. The other end of the second single mode fiber 273 is connected to an optical rotary joint 230 in the pull-back unit 102.

In contrast, the probe 101 has an adaptor 101*a* for connecting the pull-back unit 102. The probe 101 is stably held by the pull-back unit 102 by connecting the probe 101 to the pull-back unit 102 using the adaptor 101*a*. Furthermore, an end portion of a third single mode fiber 274 which is rotatably accommodated in the probe 101 is connected to the optical rotary joint 230. As a result, the second single mode fiber 273 and the third single mode fiber 274 are optically bound to each other. The other end (on a leading portion side of the probe 101) of the third single mode fiber 274 is provided with the imaging core 250 which is equipped with an optical transmitting and receiving unit which is constituted of a mirror and a lens in which light is emitted in a direction approximately orthogonal to a rotation axis.

As a result, the light emitted from the wavelength swept light source 203 is guided to the imaging core 250 which is provided at the end portion of the third single mode fiber 274 through the first single mode fiber 271, the second single mode fiber 273, and the third single mode fiber 274. The optical transmitting and receiving unit of the imaging core 250 emits the light in the direction orthogonal to the axis of the fibers and receives reflected light thereof. The received reflected light is then reversely guided so as to return to the image processing apparatus 103.

In contrast, an optical path length adjustment mechanism 220 which finely adjusts the optical path length of reference light is provided at an end portion opposite to the fourth single mode fiber 275 which is bound by the optical fiber coupler 272.

The optical path adjustment mechanism 220 functions as an optical path length changing section which is configured to change the optical path length corresponding to the variation in the length of individual probe 101 so that the variation in the length of the individual probe can be absorbed in a case where the probe 101 is replaced or the like. For this reason, a collimating lens 225 positioning at an end portion of the fourth single mode fiber 275 is provided on a movable one-axis stage 224 as shown by an arrow 226 in an optical axis direction of the collimating lens.

In accordance with an exemplary embodiment, for example, the one-axis stage 224 functions as an optical path length changing section which is configured to have a variable range of the optical path length enough to be able to absorb the variation in the optical path length in the probe 101 when the probe 101 is replaced. Furthermore, the one-axis stage 224 also has a function as an adjustment section that is configured to adjust an offset. For example, even in a case where a distal end of the probe 101 does not come into close contact with the surface of a biological tissue, a state can be set in which reference light is allowed to interfere with reflected light from a position of the surface of the biological tissue by minutely changing the optical path length of the reference light using the one-axis stage.

Light, of which the optical path length is finely adjusted by the one-axis stage 224 and which is reflected by a mirror 223 through a grating 221 and a lens 222, is guided to the fourth single mode fiber 275 again. The guided light is mixed with light, which is obtained from the second single mode fiber 273 side, by the optical fiber coupler 272 and is then received by a photodiode 204 as interference light.

The interference light which has been received by the photodiode 204 in this manner is photo-electrically converted and amplified by an amplifier 205, and is then input to a demodulator 206. Demodulation processing in which only a signal component of the interfered light is extracted is performed in the demodulator 206 and the output is input to an A/D convertor 207 as an interference light signal.

In the A/D convertor 207, the interference light signal is sampled by, for example, 2048 points at 90 MHz to generate digital data (interference light data) of one line. Note that the sampling frequency can be set to, for example, 90 MHz on the assumption that about 90% of the period (25 μsec) of the wavelength sweep is extracted as digital data of 2048 points when the repetition frequency of the wavelength sweep is set to, for example, 40 kHz, and the present disclosure is not particularly limited thereto.

The interference light data in a line unit which has been generated by the A/D convertor 207 is input to the signal processing unit 201 and is temporarily stored in the memory 202. Moreover, in the signal processing unit 201, the interference light data is frequency-resolved through FFT (fast Fourier transformation) to generate data (line data) in a depth direction. An optical tomographic image is constructed at each position in a blood vessel by coordinate-converting the generated data and is output to the display apparatus 113 at a predetermined frame rate.

The signal processing unit 201 is further connected to a drive unit for optical path length adjustment 209 and a communication unit 208. The signal processing unit 201 performs control (optical path length control) of the position of the one-axis stage 224 through the drive unit for optical path length adjustment 209.

The communication unit 208 incorporates several drive circuits and communicates with the pull-back unit 102 under the control of the signal processing unit 201. Specific examples of the communication include supply of a drive signal for rotating the third single mode fiber 274, to a radial scanning motor, using the optical rotary joint in the pull-back unit 102, reception of a signal for detecting a rotational position of the radial scanning motor, from an encoder unit 242, and supply of a drive signal for pulling the third single mode fiber 274 at a predetermined speed, to a linear drive unit 243.

Note that the previously mentioned processing in the signal processing unit 201 is realized using a predetermined program which is executed by a computer.

In the aforesaid configuration, the probe 101 is positioned at a blood vessel position (coronary artery or the like) of a patient which is to be diagnosed, and a transparent flush solution is discharged into the blood vessel through a guiding catheter toward the distal end of the probe 101 through an operation of a user. This is performed in order to exclude the influence of blood. Moreover, when a user inputs an instruction for starting scanning, the signal processing unit 201 drives the wavelength swept light source 203 and drives the radial scanning motor 241 and the linear drive unit 243 (hereinafter, referred to as emission of light and scanning of light receiving processing using the radial scanning motor 241 and the linear drive unit 243). As a result, the wavelength swept light from the wavelength swept light source 203 is supplied to the imaging core 250 through the previously mentioned route. At this time, the imaging core 250 which is positioned at the distal end of the probe 101 moves along a rotation axis while rotating. Therefore, the imaging core 250 performs emission of light to the lumen surface of a blood vessel and reception of reflected light thereof while rotating and moving along a blood vessel axis.

Figure 3:
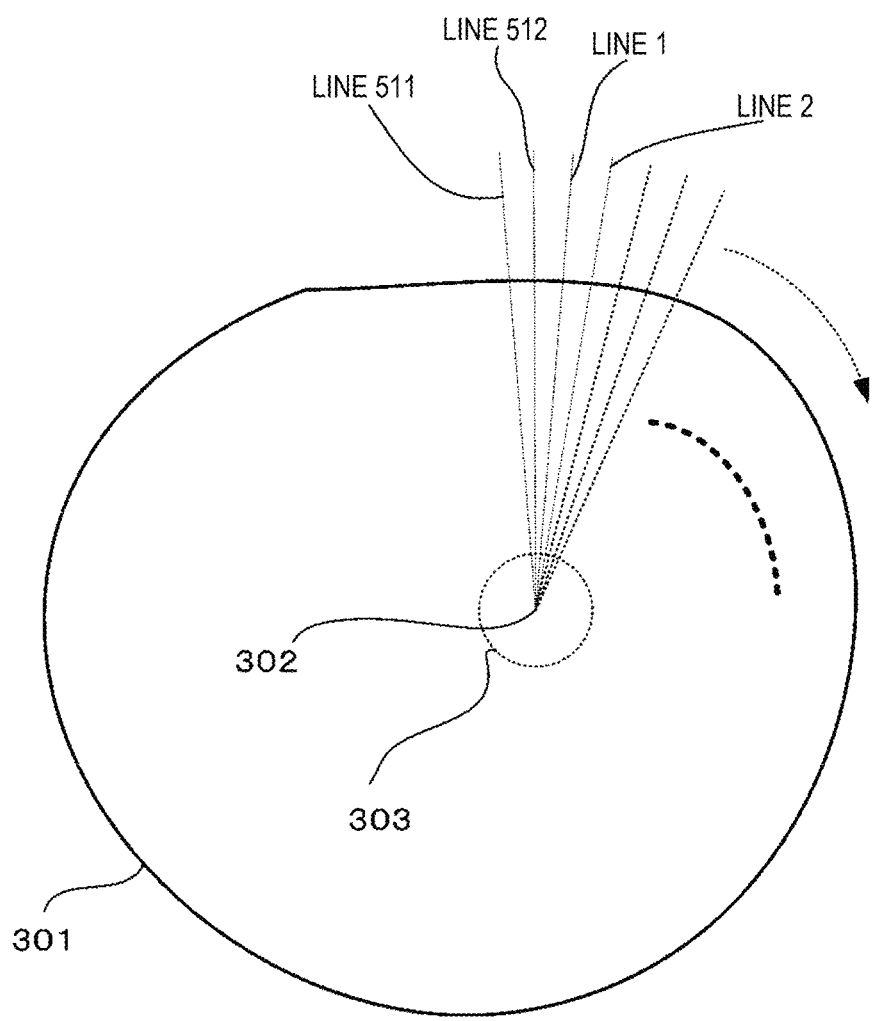
FIG. 3 is a view for illustrating reconstitution processing of a tomographic image according to the exemplary embodiment of the present disclosure.

Here, processing for generating one optical tomographic image will be simply described using FIG. 3. The drawing is a view for illustrating reconstitution processing of a tomographic image of a lumen surface 301 of a blood vessel on which the imaging core 250 is positioned. A plurality of times of transmission and reception of measurement light are performed during one rotation (360 degrees) of the imaging core 250. Through one time of the transmission and reception of light, data of one line can be obtained in a direction in which the light is emitted. Accordingly, 512 lines of data extending radially from a rotation center 302 can be obtained by performing, for example, 512 times of the transmission and reception of light during one rotation. The data of 512 lines are close to each other in the vicinity of the rotation center position and are sparse to each other as the data are separated from the rotation center position. Pixels in the vacant space between lines can be generated by performing known interpolation processing and two-dimensional tomographic images, which are visible by a human, are generated.

Figure 4:
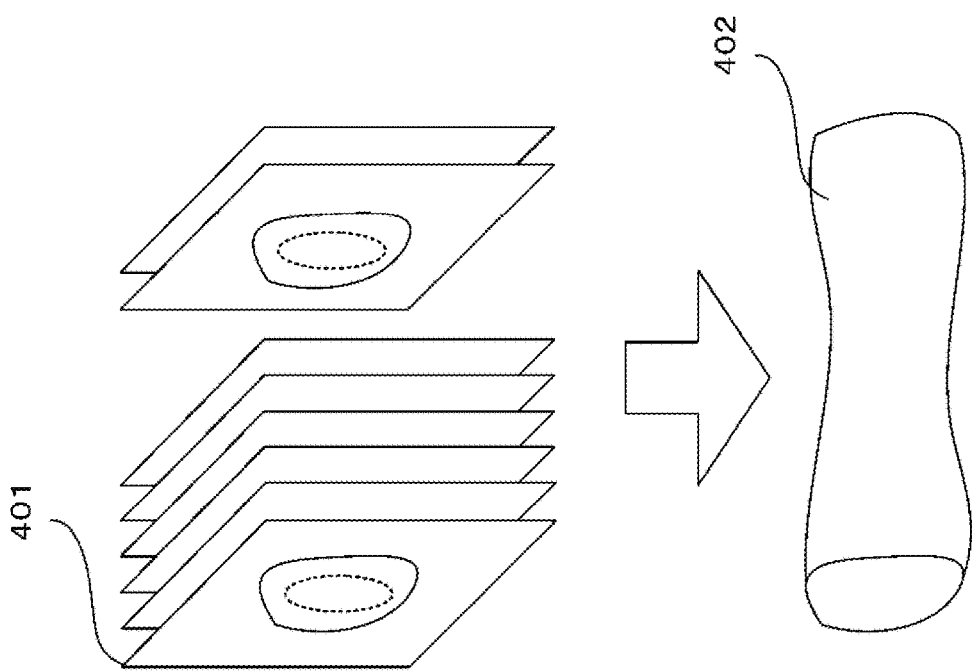
FIG. 4 is a view showing an example of reconstituted three-dimensional model data of a blood vessel according to the exemplary embodiment of the present disclosure.

As shown in FIG. 4, a three-dimensional blood vessel image 402 can be obtained by connecting the generated two-dimensional tomographic images 401 to each other along the blood vessel axis. The central position of the two-dimensional tomographic images is coincident with the rotation center position of the imaging core 250. However, it should be noted that the central position of the two-dimensional tomographic images is not coincident with the central position of the cross section of the blood vessel. Although the influence is small, light can be reflected by the surface of the lens of the imaging core 250 and the surface of the catheter, and therefore, several concentric circles are generated with respect to the rotation center axis as shown by the reference numeral 303 in the drawing.

Next, a configuration for forming an image using an ultrasound and the processing content thereof will be described. Scanning using an ultrasound is simultaneously performed with the aforesaid scanning of the light interference. In accordance with an exemplary embodiment, for example, emission of an ultrasound from the ultrasound transmitting and receiving unit, which is accommodated in the imaging core 250, and detection of a reflected wave are performed in the meantime the imaging core 250 moves in a catheter sheath of the probe 101 while rotating. For this reason, it is necessary to generate a drive signal for driving the ultrasound transmitting and receiving unit which is accommodated in the imaging core 250 and to receive a detection signal of the ultrasound output by the ultrasound transmitting and receiving unit. The transmission of the drive signal and the reception of the detected signal are performed by an ultrasound transmission and reception control unit 232. The ultrasound transmission and reception control unit 232 and the imaging core 250 are connected to each other through signal line cables 281, 282, and 283. Since the imaging core 250 rotates, the signal line cables 282 and 283 are electrically connected to each other through a slip ring 231 which is provided in the pull-back unit 102. Note that, in the drawing, the signal line cables 281 to 283 seem to be connected to each other in one line, but in fact, they accommodate a plurality of signal lines.

The ultrasound transmission and reception control unit 232 is operated under the control of the signal processing unit 201 and drives the ultrasound transmitting and receiving unit which is accommodated in the imaging core 250 to generate an ultrasound pulse wave. The ultrasound transmitting and receiving unit converts a reflected wave from a vascular tissue into an electrical signal which is then supplied to the ultrasound transmission and reception control unit 232. The ultrasound transmission and reception control unit 232 outputs the received ultrasound signal to an amplifier 233 for amplification. Then, the amplified ultrasound signal is supplied to the signal processing unit 201 as ultrasound data through a wave detector 234 and an A/D convertor 235, and is temporarily stored in the memory 202. Note that in the A/D convertor 235, the ultrasound signal which has been output by the wave detector 234 is sampled by 200 points at, for example, 30.6 MHz to generate digital data (ultrasound data) of one line. Note that the sampling frequency is set to 30.6 MHz herein which is a value calculated on the assumption that the ultrasound signal is sampled by 200 points with respect to the depth of 5 mm when the speed of sound is set to 1530 m/sec. Accordingly, the sampling frequency is not particularly limited thereto.

The signal processing unit 201 generates an ultrasound image at each position in a blood vessel by converting the ultrasound data which is stored in the memory 202 into a gray scale.

3. Processing Executed by Imaging Apparatus for Diagnosis (Particularly Image Processing Apparatus)

Next, processing executed by the imaging apparatus for diagnosis 100 (particularly image processing apparatus 103) according to the present embodiment will be described while referring to FIGS. 5 and 6.

Figure 5:
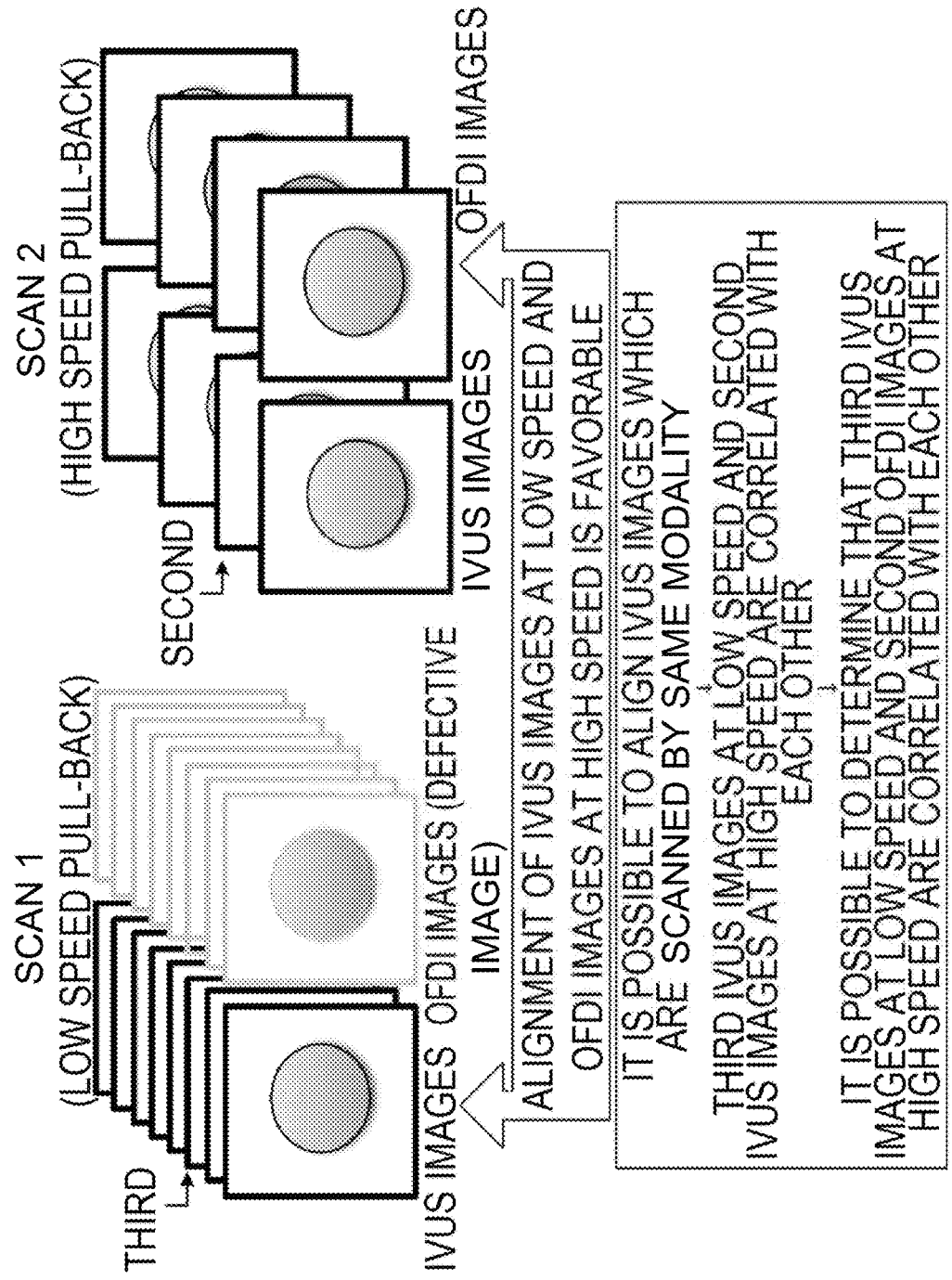
FIG. 5 is a view for illustrating image alignment according to the exemplary embodiment of the present disclosure.

FIG. 5 is a view for illustrating image alignment according to the present embodiment. The left side of FIG. 5 shows a series of IVUS images and a series of OFDI images which are acquired by scan 1 (low speed pull-back: for example, 0.5 mm/sec) through operations of the optical transmitting and receiving unit and the ultrasound transmitting and receiving unit which are accommodated in the imaging core 250. Moreover, the right side of FIG. 5 shows a series of IVUS images and a series of OFDI images which are acquired by scan 2 (high speed pull-back: for example, 20 mm/sec) through operations of the optical transmitting and receiving unit and the ultrasound transmitting and receiving unit which are accommodated in the imaging core 250. Frame images acquired by the scan through high speed pull-back are sparse to each other than those acquired by the scan through low speed pull-back.

Here, in many cases, the OFDI images acquired by scan 1 (low speed pull-back) become defective during scan since, in some cases, the retention of a flush solution is disconnected. Alignment of the IVUS images acquired through low speed pull-back and the OFDI images acquired through high speed pull-back is favorable. However, it is impossible to align the images as they are since the images are scanned by different modalities.

In contrast, the IVUS images which are scanned by the same modality can be aligned. Selection of corresponding images is received from a user through display of a series of IVUS images acquired through low speed pull-back and a series of IVUS images acquired through high speed pull-back, on the display apparatus 113. For example, as shown in FIG. 5, a user visually confirms and selects that the third IVUS images which are acquired through low speed pull-back and the second IVUS images which are acquired through high speed pull-back. Through the selection of the user, the third IVUS images which are acquired through low speed pull-back and the second IVUS images which are acquired through high speed pull-back are correlated with each other. As a result, a series of the third IVUS images which are acquired through low speed pull-back and a series of second OFDI images which are acquired through high speed pull-back can be correlated with each other, and therefore, these images can be displayed on the display apparatus 113.

Figure 6:
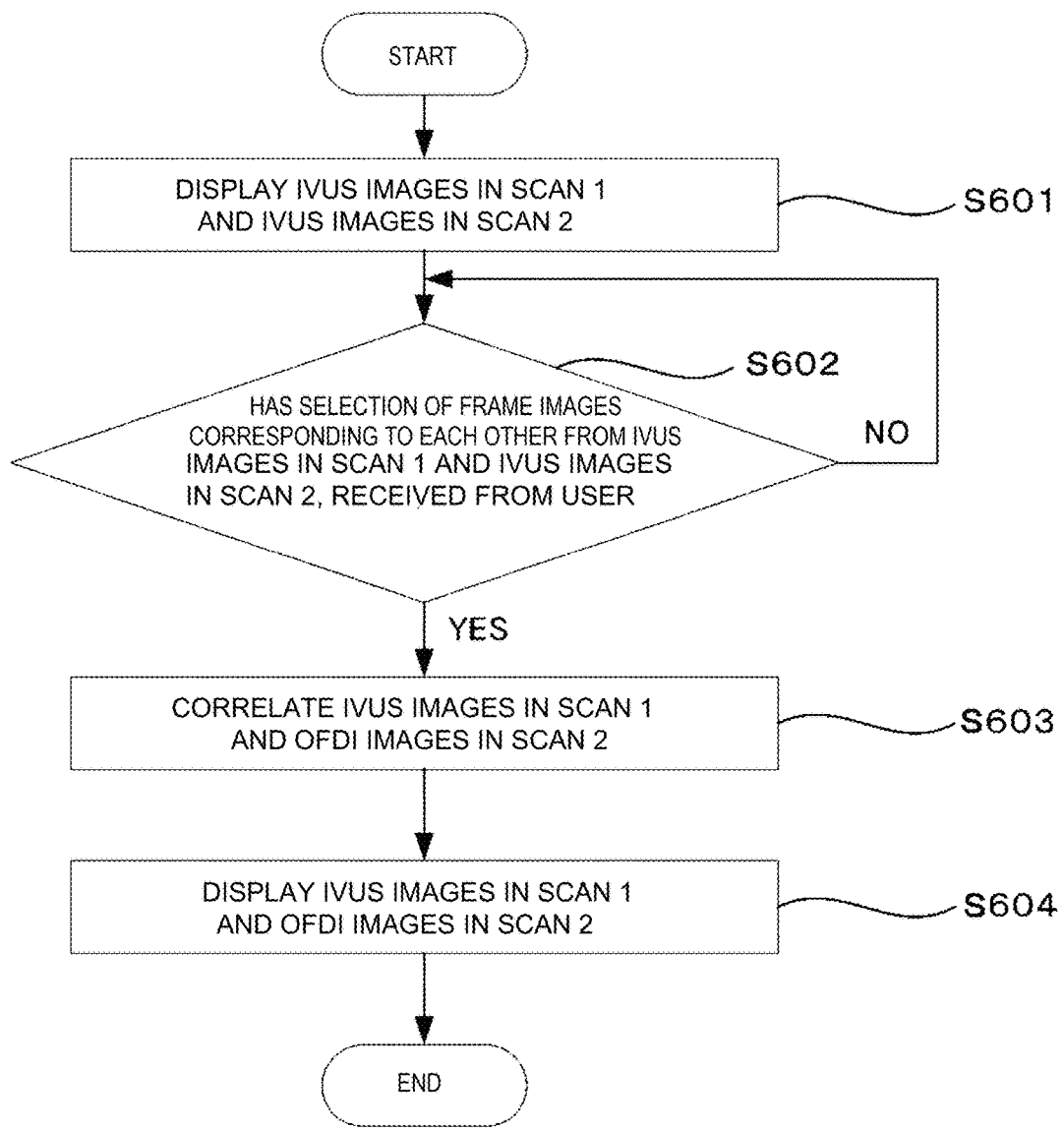
FIG. 6 is a flowchart showing a processing procedure of image alignment (alignment of IVUS images in scan 1 and OFDI images in scan 2) according to a first exemplary embodiment.

In accordance with an exemplary embodiment, a more specific procedure is shown in FIG. 6. FIG. 6 is a flowchart showing a processing procedure of image alignment (alignment of IVUS images in scan 1 and OFDI images in scan 2) according to a first exemplary embodiment.

In S601, the control unit 2011 of the image processing apparatus 103 displays a series of the IVUS images which are acquired through the image acquisition unit 2010 through scan 1 and a series of IVUS images which are acquired through the image acquisition unit 2010 through scan 2 on the display apparatus 113. Here, the scan 1 is scan of IVUS images and OFDI images acquired through low speed pull-back and the scan 2 is scan of IVUS images and OFDI images acquired through high speed pull-back.

In S602, the selection reception unit 2012 of the image processing apparatus 103 determines whether the selection reception unit has received a selection of frame images corresponding to each other from the IVUS images which are acquired through scan 1 and the IVUS images which are acquired through scan 2, from a user. For example, a user selects the third IVUS images acquired through scan 1 and the second IVUS images acquired through scan 2. Note that the selection operation of a user may be performed through the operation panel 112 or the mouse 114, or the display apparatus 113 may be performed through a touch operation as long as the display apparatus 113 has a touch panel function.

When a selection of frame images corresponding to each other is received from a user, the process proceeds to S603. In contrast, when there is no selection of frame images corresponding to each other which are received from a user, the apparatus waits until there is an input. When a user cannot visually find the frame images corresponding to each other, a screen indicating "Corresponding frame images cannot be found . . . . The processing is completed . . . . YES/NO" may be displayed on the display apparatus 113 after the lapse of a predetermined time, to complete the processing in accordance with a YES selection of the user. Alternately, a configuration may be employed such that the screen is displayed from the beginning and an operation for completing the processing is received from a user at an arbitrary timing.

In S603, the control unit 2011 of the image processing apparatus 103 correlates a series of the IVUS images which are acquired through scan 1 with a series of the OFDI images which are acquired through scan 2, based on the selection of a user in S602.

In S604, the control unit 2011 of the image processing apparatus 103 displays a series of the IVUS images which are acquired through scan 1 and a series of the OFDI images which are acquired through scan 2, on the display apparatus 113 in a form in which a user can recognize the correspondence relation. For example, the display apparatus 113 displays the third IVUS images which are acquired through scan 1 on the left side of the screen and displays the second OFDI images which are acquired through scan 2 on the right side of the screen. When a user changes an image to an N-th image, another image is changed to a corresponding M-th image for display. In the above, each processing in FIG. 6 is completed.

Accordingly, it can be relatively easy to align the images using different modalities, and therefore, a user can evaluate an identical observation object using high-quality images.

Note that in the example in FIG. 6, the correlation of the IVUS images which are acquired through scan 1 and the IVUS images which are acquired through scan 2 is performed by receiving a selection of frame images corresponding to each other, from a user. In contrast, the signal processing unit 201 of the image processing apparatus 103 may further include a correlation unit, and the correlation unit may have a configuration in which the image characteristics of a series of IVUS images which are acquired through scan 1 and a series of IVUS images which are acquired through scan 2 are extracted and images of which the image characteristics are substantially coincident with each other are automatically correlated with each other. For example, the correlation unit can automatically perform the correlation using the signal processing unit 201, which extracts a lumen region of a blood vessel from images acquired through scan 1 and scan 2, and by detecting a characteristic position of a vascular bifurcated portion or the like. In addition, the correlation unit can automatically perform the correlation using the signal processing unit 201 which performs quantification of the similarity with respect to the images acquired through scan 1 and scan 2, using a technique such as matching of the similarity of the images acquired through scan 1 and scan 2.

In addition, the scan 1 is set to scanning through low speed pull-back and the scan 2 is set to scanning through high speed pull-back. However, the same processing is applicable even in a case where the alignment of the OFDI images acquired through scan 1 and the IVUS images acquired through scan 2 is performed by setting the scan 1 as scan through high speed pull-back and setting the scan 2 as scan through low speed pull-back.

In addition, when correlating a series of the IVUS images which are acquired through scan 1 with a series of the OFDI images which are acquired through scan 2, the correlation is performed by considering the conditions of scan (the pull-back speed in the scan 1 and the scan 2) as well.

Also in the second embodiment, similarly to the first embodiment, an example of performing alignment of OFDI images which are acquired through scan 1 (low speed pull-back) and IVUS images which are acquired through scan 2 (high speed pull-back) will be described. The configuration of the apparatus in the second embodiment is the same as that in the first embodiment, and therefore, the description thereof will not be repeated.

Figure 7:
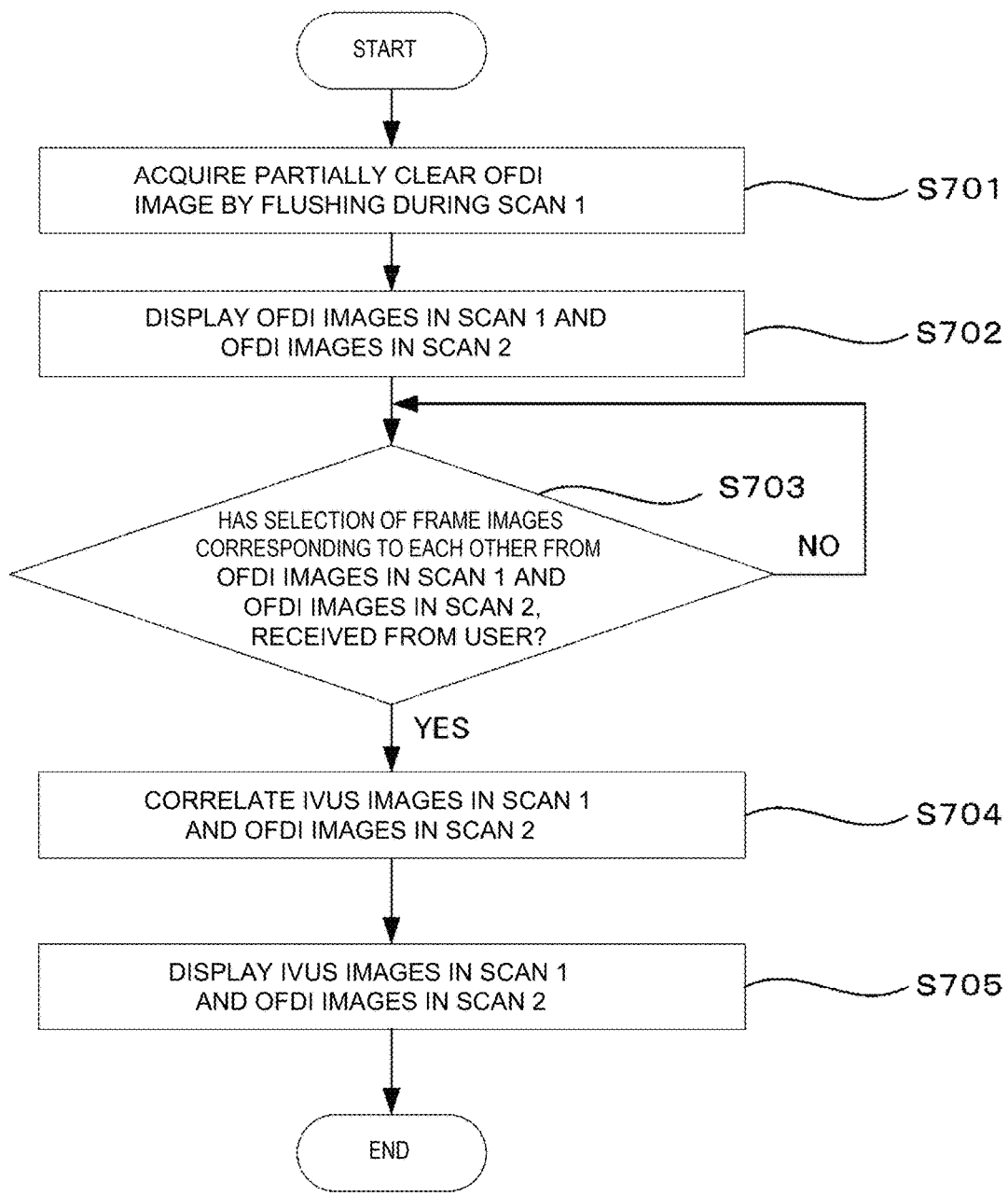
FIG. 7 is a flowchart showing a processing procedure of image alignment (alignment of IVUS images in scan 1 and OFDI images in scan 2) according to a second exemplary embodiment.

FIG. 7 is a flowchart showing a processing procedure of image alignment (alignment of IVUS images in scan 1 and OFDI images in scan 2) according to the present exemplary embodiment.

In S701, the control unit 2011 of the image processing apparatus 103 performs control so as to perform flush during the scan 1 and scans OFDI images which are partially clear. Here, similarly to the first embodiment, the scan 1 is scan of IVUS images and OFDI images acquired through low speed pull-back and the scan 2 is scan of IVUS images and OFDI images acquired through high speed pull-back.

In S702, the control unit 2011 of the image processing apparatus 103 displays a series of OFDI images which are acquired through the image acquisition unit 2010 through scan 1 and a series of OFDI images which are acquired through the image acquisition unit 2010 through scan 2, on the display apparatus 113.

In S703, the selection reception unit 2012 of the image processing apparatus 103 determines whether the selection reception unit has received a selection of frame images corresponding to each other from the OFDI images which are acquired through scan 1 and the OFDI images which are acquired through scan 2, from a user. When a selection of frame images corresponding to each other is received from a user, the process proceeds to S704. In contrast, in a case where the selection of frame images corresponding to each other is not received from a user, the unit waits until there is an input.

In S704, the control unit 2011 of the image processing apparatus 103 correlates a series of IVUS images which are acquired through scan 1 with a series of OFDI images which are acquired through scan 2 based on the selection of a user in S703.

In S705, the control unit 2011 of the image processing apparatus 103 displays a series of the IVUS images which are acquired through scan 1 and a series of the OFDI images which are acquired through scan 2, on the display apparatus 113 in a form in which a user can recognize the correspondence relation. In the above, each processing in FIG. 7 is completed.

As described above, in the present exemplary embodiment, partially clear OFDI images are scanned by performing a flush operation even during the scan 1 (low speed pull-back), and the OFDI images in the scan 1 (low speed pull-back) and the OFDI images in the scan 2 (high speed pull-back) are displayed. Similarly to the first embodiment, the IVUS images in the scan 1 (low speed pull-back) and the OFDI images in the scan 2 (high speed pull-back) are finally displayed in a form in which a user can recognize the correspondence relation, by performing the correlation based on the selection of a user.

Accordingly, it can be relatively easy to align the images using different modalities, and therefore, a user can evaluate an identical observation object using high-quality images.

Note that the signal processing unit 201 of the image processing apparatus 103 may further include a correlation unit, and the correlation unit may have a configuration in which the image characteristics of a series of OFDI images which are acquired through scan 1 and a series of OFDI images which are acquired through scan 2 are extracted and images of which the image characteristics are substantially coincident with each other are automatically correlated with each other. For example, the correlation unit can automatically perform the correlation using the signal processing unit 201, which extracts a lumen region of a blood vessel from images acquired through scan 1 and scan 2, and by detecting a characteristic position of a vascular bifurcated portion or the like. In addition, the correlation unit can automatically perform the correlation using the signal processing unit 201 which performs quantification of the similarity with respect to the images acquired through scan 1 and scan 2, using a technique such as matching of the similarity of the images acquired through scan 1 and scan 2. In addition, the same processing is applicable even in a case where the alignment of the OFDI images acquired through scan 1 and the IVUS images acquired through scan 2 is performed by setting the scan 1 as scan through high speed pull-back and setting the scan 2 as scan through low speed pull-back.

In the third exemplary embodiment, when scanning IVUS images and OFDI images, radiation images (for example, X-ray fluoroscopic images) are scanned together. Radiation images which are acquired during scan 1 (low speed pull-back) and radiation images which are acquired during scan 2 (high speed pull-back) are displayed, and similarly to the first and second embodiments, IVUS images in the scan 1 (low speed pull-back) and OFDI images in the scan 2 (high speed pull-back) are finally correlated with each other for display, by performing the correlation based on the selection of a user.

First, the image processing apparatus 103 according to the present exemplary embodiment and a configuration example of peripheral devices thereof will be described while referring to FIG. 8.

The basic configuration of the apparatus is the same as the configuration described in the first and second embodiments. However, the image processing apparatus 103 according to the present embodiment is connected to a radiography apparatus 802, and a photographing control unit 801 which is included in the image processing apparatus 103 controls a photographing operation of the radiography apparatus.

The photographing control unit 801 is connected to the signal processing unit 201. Note that the image acquisition unit 2010 according to the present embodiment also acquires a series of radiation images which are photographed by the radiography apparatus 802.

Radiation images are acquired by the radiography apparatus 802 in synchronization with scan of IVUS images and OFDI images using the imaging core 250. In addition, the selection reception unit 2012 according to the present exemplary embodiment receives a selection of the radiation images based on an input from a user.

Here, a marker is provided at a distal portion of the imaging core 250 and radiographing is performed by the imaging core 250, and therefore, the position of the marker can be observed.

Here, FIG. 9 is a view illustrating a relationship between a radiation image and an image which is scanned by the imaging core 250. In FIG. 9, the reference numeral 901 is a series of images (IVUS images or OFDI images) which are scanned by the imaging core 250, and the reference numerals 902 and 903 are radiation images. The reference numeral 904 is a marker provided in the imaging core 250. The position of the imaging core 250 can be observed since the marker 904 is reflected on the radiation images. The correspondence relation between the images scanned by the imaging core 250 and the radiation images is already known by photographing the radiation images in synchronization with the IVUS images and the OFDI images acquired by the imaging core 250. Accordingly, a selection of corresponding images is received from a user through display of the radiation images which are acquired during scan 1 (low speed pull-back) and radiation images which are acquired during scan 2 (high speed pull-back), on the display apparatus 113. Then, IVUS images which are acquired by the scan 1 (low speed pull-back) and OFDI images which are acquired by the scan 2 (high speed pull-back) are correlated with each other for display based on the selection of a user.

As shown in FIG. 9, the first image (IVUS image or OFDI image) which is scanned by the imaging core 250 corresponds to the radiation image 902 and the sixth image (IVUS image or OFDI image) corresponds to the radiation image 903.

The correspondence relation between the IVUS image, the OFDI image, and the radiation image which are acquired through scan 1 (low speed pull-back) is already known. In addition, the correspondence relation between the IVUS image, the OFDI image, and the radiation image which are acquired through scan 2 (high speed pull-back) is already known. Accordingly, an IVUS image of the scan 1 can be correlated with an OFDI image of the scan 2 for display by correlating a radiation image of scan 1 with a radiation image of scan 2.

Subsequently, FIG. 10 is a flowchart showing a processing procedure of image alignment (alignment of IVUS images in scan 1 and OFDI images in scan 2) according to the present exemplary embodiment.

In S1001, the photographing control unit 801 of the image processing apparatus 103 controls the radiography apparatus 802 to photograph a series of radiation images in synchronization with acquisition of IVUS images and OFDI images in the scan 1 (low speed pull-back) and the scan 2 (high speed pull-back).

In S1002, the control unit 2011 of the image processing apparatus 103 displays a series of radiation images which are acquired through scan 1 and a series of radiation images which are acquired through scan 2, on the display apparatus 113.

In S1003, the selection reception unit 2012 of the image processing apparatus 103 determines whether the selection reception unit has received a selection of frame images corresponding to each other from the radiation images which are acquired through scan 1 and the radiation images which are acquired through scan 2, from a user. When a selection of frame images corresponding to each other is received from a user, the process proceeds to S1004. In contrast, when there is no selection of frame images corresponding to each other which are received from a user, the apparatus waits until there is an input.

In S1004, the control unit 2011 of the image processing apparatus 103 correlates a series of the IVUS images which are acquired through scan 1 with a series of the OFDI images which are acquired through scan 2, based on the selection of a user in S1003.

In S1005, the control unit 2011 of the image processing apparatus 103 displays a series of the IVUS images which are acquired through scan 1 and a series of the OFDI images which are acquired through scan 2, on the display apparatus 113 in a form in which a user can recognize the correspondence relation. In the above, each processing in FIG. 10 is completed.

As described above, in the present embodiment, the radiation images are acquired in synchronization with scan of the IVUS images and the OFDI images. Then, the IVUS images acquired through the scan 1 (low speed pull-back) and the OFDI images acquired through the scan 2 (high speed pull-back) are correlated with each other using the radiation images and are displayed to a user.

Accordingly, it can be relatively easy to align the images using different modalities, and therefore, a user can evaluate an identical observation object using high-quality images.

Note that, similarly to the first and the second embodiments, the signal processing unit 201 of the image processing apparatus 103 may further include a correlation unit, and the correlation unit may have a configuration in which the image characteristics of a series of IVUS images which are acquired through scan 1 and a series of IVUS images which are acquired through scan 2 are extracted and images of which the image characteristics are substantially coincident with each other are automatically correlated with each other.

The embodiments of the present disclosure have been described through the first to third exemplary embodiments. However, the present disclosure can be applied to various cases, for example, alignment of IVUS images using OFDI images, alignment of radiation images using OFDI images, alignment of OFDI images using IVUS images, alignment of radiation images using IVUS images, alignment of IVUS images using radiation images, and alignment of OFDI images using radiation images.

As can be seen from the above-described embodiments, the processing according to the present exemplary embodiments is controlled by the signal processing unit 201 constituted of a microprocessor. The function of the microprocessor is realized by executing a program. Therefore, as a matter of course, the program thereof is within the category of the present disclosure. In addition, in general, the program is stored in a computer-readable storage medium such as a CD-ROM, a DVD-ROM or the like, and is executable by being set in a reading device (such as a CD-ROM drive or the like) which is possessed by a computer, and by being copied or installed in a system. Therefore, it is obvious that the computer-readable storage medium is also within the category of the present disclosure.

The detailed description above describes an image processing apparatus, a method of controlling the image processing apparatus, a program, and a storage medium. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An image processing apparatus which processes an image of a target object, comprising:
    a computer processor configured to:
        acquire a series of first images with a first imaging modality and a series of second images with a second imaging modality of the target object, wherein each of the series of the first images and the series of the second images are scanned both at a first pull-back speed and at a second pull-back speed faster than the first pull-back speed;
        correlate the series of the first images, which are scanned at the second pull-back speed, with the series of the second images, which are scanned at the second pull-back speed;
        correlate one of the first images, which are scanned at the first pull-back speed, with one of the first images, which are scanned at the second pull-back speed; and
        correlate and align the series of the first images which are scanned at the first pull-back speed and the series of the second images which are scanned at the second pull-back speed based on a result of the correlation of the one of the first images which are scanned at the first pull-back speed and the one of the first images which are scanned at the second pull-back speed and a result of the correlation of the series of the first images which are scanned at the second pull-back speed and the series of the second images which are scanned at the second pull-back speed; and
    a display apparatus configured to display the images based on a result of the correlation and alignment of the series of the first images which are scanned at the first pull-back speed and the series of the second images which are scanned at the second pull-back speed.

2. The image processing apparatus according to claim 1, wherein the computer processor is configured to:
    display the series of the first images which are scanned at the first pull-back speed and the series of the first images which are scanned at the second pull-back speed, on the display apparatus;
    receive a selection of the first images which are scanned at the first pull-back speed and the first images which are scanned at the second pull-back speed, from the images displayed on the display apparatus, from a user; and
    perform the correlation based on the selection.

3. The image processing apparatus according to claim 1, wherein
    the first images are ultrasound tomographic images of the target object; and
    the second images are optical tomographic images of the target object.

4. The image processing apparatus according to claim 1, wherein
    the first images are optical tomographic images of the target object;
    the second images are ultrasound tomographic images of the target object; and
    the first images are acquired by performing a flush operation during scanning at the first pull-back speed.

5. The image processing apparatus according to claim 1, wherein the target object is a blood vessel.

6. An image processing apparatus which processes an image of a target object, comprising:
    a computer processor configured to:
        acquire a series of first images of the target object with a first imaging modality and a series of second images with a second imaging modality of the target object, wherein each of the series of the first images and the series of the second images are scanned both at a first pull-back speed and at a second pull-back speed faster than the first pull-back speed;
        acquire a series of third images with a third imaging modality of the target object which are scanned in synchronization with the series of the first images and the series of the second images;
        correlate one of the third images, which are scanned at the first pull-back speed, with one of the third images, which are scanned at the second pull-back speed; and
        correlate and align the series of the first images which are scanned at the first pull-back speed and the series of the second images which are scanned at the second pull-back speed based on a result of the correlation of the one of the third images which are scanned at the first pull-back speed and the one of the third images which are scanned at the second pull-back speed; and
    a display apparatus configured to display the images based on a result of the correlation and alignment of the series of the first images which are scanned at the first pull-back speed and the series of the second images which are scanned at the second pull-back speed.

7. The image processing apparatus according to claim 6, wherein the computer processor is configured to:
    display the series of the third images which are scanned at the first pull-back speed and the series of the third images which are scanned at the second pull-back speed, on the display apparatus;
    receive a selection of the third images which are scanned at the first pull-back speed and the corresponding third images which are scanned at the second pull-back speed, from the images displayed on the display apparatus, from a user; and
    perform the correlation based on the selection.

8. The image processing apparatus according to claim 6, wherein
    the first images are ultrasound tomographic images of the target object;

the second images are optical tomographic images of the target object; and the third images are radiation images of the target object.

9. The image processing apparatus according to claim 6, wherein the first images are optical tomographic images of the target object;

the second images are ultrasound tomographic images of the target object; and the third images are radiation images of the target object.

10. The image processing apparatus according to claim 8, wherein the radiation images of the target object include a marker which is provided in an imaging core which scans the ultrasound tomographic images and the optical tomographic images of the target object.

11. The image processing apparatus according to claim 6, wherein the target object is a blood vessel.

12. A method of controlling an image processing apparatus which processes an image of a target object, the method comprising:

acquiring a series of first images with a first imaging modality and a series of second images with a second imaging modality of the target object, wherein each of the series of the first images and the series of the second images are scanned both at a first pull-back speed and at a second pull-back speed faster than the first pull-back speed;

correlating the series of the first images, which are scanned at the second pull-back speed, with the series of the second images, which are scanned at the second pull-back speed;

correlating one of the first images, which are scanned at the first pull-back speed, with one of the first images, which are scanned at the second pull-back speed;

correlating and aligning the series of the first images which are scanned at the first pull-back speed and the series of the second images which are scanned at the second pull-back speed based on a result of the correlation of the one of the first images which are scanned at the first pull-back speed and the one of the first images which are scanned at the second pull-back speed and a result of the correlation of the series of the first images which are scanned at the second pull-back speed and the series of the second images which are scanned at the second pull-back speed; and displaying the images on a display apparatus, based on a result of the correlation and alignment of the series of the first images which are scanned at the first pull-back speed and the series of the second images which are scanned at the second pull-back speed.

13. The method of controlling the image processing apparatus according to claim 12, comprising:

displaying the series of the first images which are scanned at the first pull-back speed and the series of the first images which are scanned at the second pull-back speed, on the display apparatus;

receiving a selection of the first images which are scanned at the first pull-back speed and the first images which are scanned at the second pull-back speed, from the images displayed on the display apparatus, from a user; and performing the correlation based on the selection.

14. The method of controlling the image processing apparatus according to claim 12, wherein the target object is a blood vessel.

15. A non-transitory computer readable medium having a program for causing a computer to execute each step of the method of controlling the image processing apparatus according to claim 12.

16. A method of controlling an image processing apparatus which processes an image of a target object, the method comprising:

acquiring a series of first images with a first imaging modality of the target object and a series of second images with a second imaging modality of the target object, wherein each of the series of the first images and the series of the second images are scanned both at a first pull-back speed and at a second pull-back speed faster than the first pull-back speed, and a series of third images with a third imaging modality of the target object which are scanned in synchronization with the series of the first images and the series of the second images;

correlating one of the third images, which are scanned at the first pull-back speed, with one of the third images, which are scanned at the second pull-back speed;

correlating and aligning the series of the first images which are scanned at the first pull-back speed and the series of the second images which are scanned at the second pull-back speed based on a result of the correlation of the one of the third images which are scanned at the first pull-back speed and the one of the third images which are scanned at the second pull-back speed; and displaying the images on a display apparatus, based on a result of the correlation and alignment of the series of the first images which are scanned at the first pull-back speed and the series of the second images which are scanned at the second pull-back speed.

17. The method of controlling the image processing apparatus according to claim 16, comprising:

displaying the series of the third images which are scanned at the first pull-back speed and the series of the third images which are scanned at the second pull-back speed, on the display apparatus;

receiving a selection of the third images which are scanned at the first pull-back speed and the third images which are scanned at the second pull-back speed, from the images displayed on the display apparatus, from a user; and performing the correlation based on the selection.

18. The method of controlling the image processing apparatus according to claim 16, wherein the target object is a blood vessel.

19. A non-transitory computer readable medium having a program for causing a computer to execute each step of the method of controlling the image processing apparatus according to claim 16.

20. A non-transitory computer-readable storage medium in which the method of controlling the image processing apparatus according to claim 16 is stored.

* * * * *